United States Patent [19]

Cline

[11] Patent Number: 5,047,347
[45] Date of Patent: Sep. 10, 1991

[54] GAS PERMEABLE CULTURE FLASK AND METHOD FOR CULTURING MAMMALIAN CELLS

[76] Inventor: Martin J. Cline, 441 Alma Real Dr., Pacific Palisades, Calif. 90272

[21] Appl. No.: 86,075

[22] Filed: Aug. 17, 1987

[51] Int. Cl.5 .......................................... C12M 1/24
[52] U.S. Cl. .................................. 435/296; 435/284; 220/371
[58] Field of Search .............................. 220/371–373; 215/308; 435/284, 296, 809, 818, 298

[56] References Cited

U.S. PATENT DOCUMENTS 2,950,833  8/1960  Short ..................................... 215/235
3,158,553  11/1964  Carski ................................... 435/298
4,377,247  3/1983  Hazard et al. ........................ 215/235

FOREIGN PATENT DOCUMENTS 2028082  3/1980  United Kingdom .

Primary Examiner—Noah P. Kamen

[57] ABSTRACT

A gas permeable culture flask and method for culturing mammalian cells wherein a gas permeable insert is provided in the flask to allow rapid and uniform equilibration of gases between the atmosphere of the culture flask and the atmosphere of the incubator into which the flask is placed for culturing. The size of the gas permeable insert relative to the overall surface area of the flask is limited to allow the flask to be removed from the incubator for observation, testing and culture treatment for relatively long times without substantial changes to the flask atmosphere. Alternatively, removable covers are provided for occluding passage of gases through the gas permeable insert when the flask is removed from the controlled atmosphere of the incubator.

9 Claims, 1 Drawing Sheet

U.S. Patent  Sep. 10, 1991  5,047,347
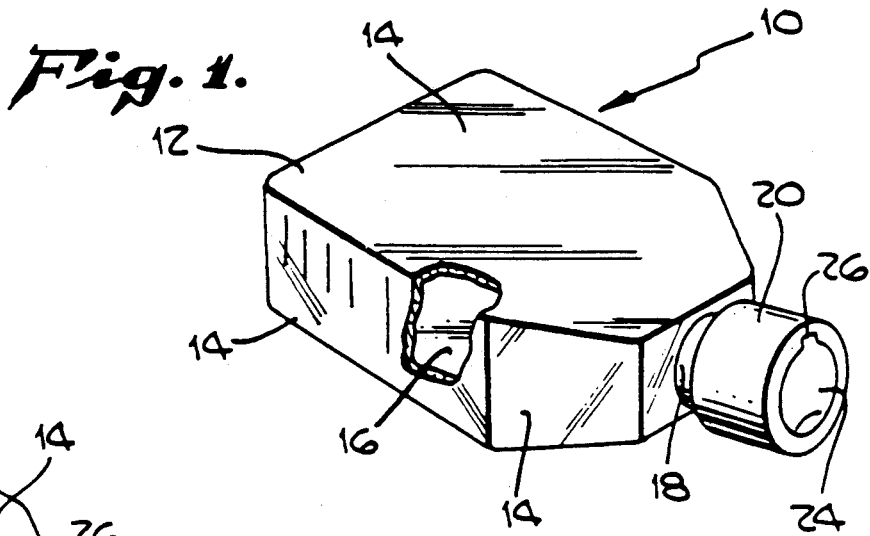
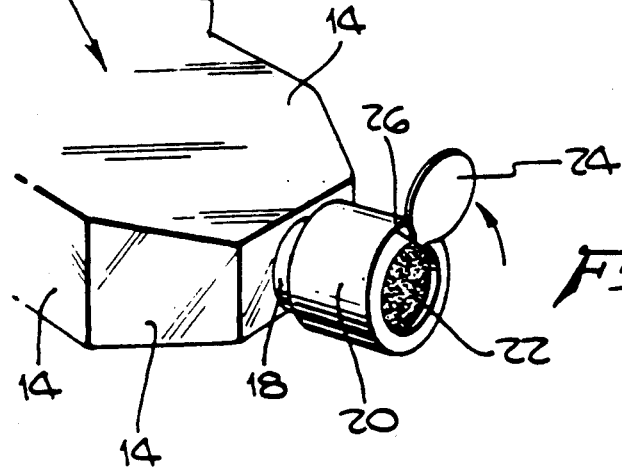
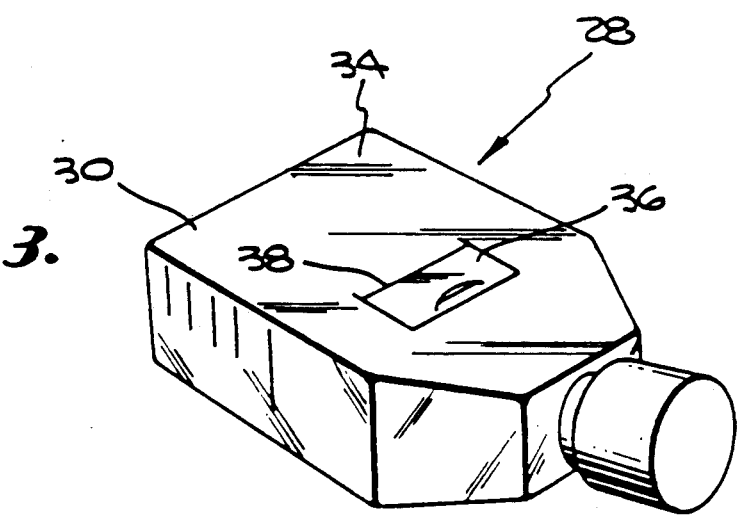
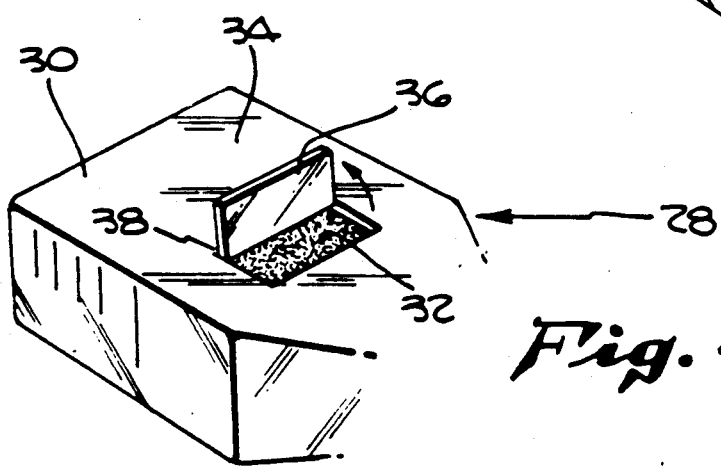

GAS PERMEABLE CULTURE FLASK AND METHOD FOR CULTURING MAMMALIAN CELLS

This application is a continuation of application Ser. No. 06/599,499, filed Apr. 12, 1984 now abandoned.

BACKGROUND OF THE INVENTION

The growth and propagation of mammalian cells in vitro (generically designated as tissue culture) is widely used in experimental biology and for the production of viral vaccines. In the future, tissue culture may find increasing use in the production of useful biological molecules generated by recombinant DNA techniques.

Typically, mammalian cells are cultured under conditions in which the hydrogen ion concentration (pH, the negative logarithm of the hydrogen ion concentration), temperature, humidity, osmolarity and concentration of certain ions are controlled within relatively narrow limits. Sterile conditions are necessary to exclude contamination and subsequent overgrowth by microorganisms.

In the vast majority of mammalian tissue culture systems in use at present, pH is maintained near physiologic levels (about pH 7.4) by utilizing a bicarbonate buffering system ($H \cdot HCO_3 \rightleftharpoons H^+ + HCO_3^-$) in the tissue culture fluid, in conjunction with an incubator in which carbon dioxide ($CO_2$) is infused at a rate sufficient to maintain a concentration in the incubator atmosphere of approximately 5 to 7 volume percent. The $CO_2$ reacts with water to form the weak acid, carbonic acid, which in turn interacts with bicarbonate ion ($HCO_3^-$) in the tissue culture fluid to form a buffering system which maintains the pH near physiologic levels. Entry of $CO_2$ from the incubator into the tissue culture flask is generally achieved by utilizing a loosely fitting cap or stopper on the culture flask so that a small open space remains for exchange of gas between flask and incubator. The limitations to this current system of cell culture are apparent (1) susceptibility to contamination by microorganisms because of gas flow through the small but unobstructed space between cap and the flask; (2) a slow and variable rate of achieving pH equilibration by diffusion of $CO_2$ through the loose-fitting cap.

In U.S. Pat. No. 3,870,602, issued on Mar. 11, 1975, a culture flask is disclosed in which the walls of the flask are made from an impact resistant polystyrene plastic which is permeable to water vapor, oxygen and carbon dioxide and impermeable to any microorganism or spores growing within the flask. This type of flask in which the walls are gas permeable is effective in preventing microorganisms from entering or exiting the flask while at the same time allowing for uniform and relatively fast equilibration between the atmosphere in the incubator and the flask.

Removal of the flask from the controlled atmosphere of the incubator is often required during growth and culturing of mammalian cells. The flasks are usually removed for inspection and/or treatment of the cells and culture fluids. It is important that the pH of the cell culture be maintained at the desired physiologic level while the flask is outside of the incubator. A problem arises when gas permeable flasks of the type described above are used in such tissue culture systems due to the rapid escape of carbon dioxide from the flask when it is removed from the controlled atmosphere of the incubator. This rapid loss of carbon dioxide through the gas permeable walls of the flask results in the pH of the cell culture rising rapidly to levels which are not suitable for optimum cell growth.

It would be desirable to provide an improved gas permeable filter flask which not only includes the features of providing rapid and uniform equilibration between the flask atmosphere and the incubator atmosphere, but also includes features which allow the culture flask to be removed from the controlled atmosphere of the incubator for reasonably long times without subjecting the cell culture to undesirable changes in the pH of the system.

SUMMARY OF THE INVENTION

In accordance with the present invention, a gas permeable culture flask and method for culturing mammalian cells is provided which allows rapid and uniform equilibration of the atmosphere in the culture flask with the controlled atmosphere of an incubator while still providing a totally closed system which prevents entry of microbial organisms into the flask. Further, the improved flask and method in accordance with the present invention allows the flask to be removed from the controlled atmosphere of the incubator and left outside for relatively long periods of time without substantial escape of gases from the flask and the resultant undesirable changes in the pH of the culture.

The present invention is based upon a flask having gas impermeable walls with a surface area defining a culturing zone having an atmosphere containing one or more gases. The flask includes a threaded opening and cap or other means for allowing introduction of mammalian cells and culture fluids into the culturing zone to form a cell culture. The flask includes a gas permeable insert located in the flask wall which defines a gas permeable opening through which the gases from the atmosphere in the incubator can communicate with the gases in the atmosphere of the flask to thereby allow equilibration between the two atmospheres while the flask is in the incubator. This allows rapid and uniform equilibration between the atmosphere in the flask and the incubator so that the flask atmosphere can be controlled to provide selected levels of gases which provide the desired growth of the cell culture.

As a particular feature of the present invention, the size of the gas permeable insert is limited to a surface area of below approximately 3% of the total surface of the area of the flask. It was discovered that gas permeable inserts with relative surface areas within this size range provided rapid and uniform equilibration of the atmospheres in the culture flask and incubator while still limiting the escape of desirable gases such as $CO_2$ from the flask when it is removed from the incubator for viewing or other culturing related activities.

As another feature of the present invention, means associated with the flask are provided for selectively occluding the gas permeable insert when the flask is removed from the incubator atmosphere to thereby prevent the escape of gases from the flask to thereby increase the amount of time the flask can be left outside the incubator while still maintaining the desired selected levels of gases and pH within the flask. When this particular feature of the present invention is utilized, the limitation of the gas permeable insert to less than approximately 3% of the overall surface area of the flask is not necessary.

The above discussed and many other features and attendant advantages of the present invention will become apparent as the invention becomes better understood by reference to the following detailed description when considered in conjunction with the accompanying drawings.

BRIEF DESCRIPTION OF THE DRAWINGS

FIG. 1 is a perspective view of a preferred embodiment of the culture flask in accordance with the present invention in which the gas permeable insert is located within the cap of the flask. The flask is shown with the cover for the gas permeable insert in the closed or occluding position.

FIG. 2 is a perspective view of the flask of FIG. 1 showing the gas permeable insert cover in the open position.

FIG. 3 is a perspective view of a second preferred embodiment in which the gas permeable insert is located in a wall of the flask. The flask shown in FIG. 3 includes a cover for the gas permeable insert which is shown in the closed or occluding position.

FIG. 4 is a perspective view of the flask shown in FIG. 3 in which the gas permeable insert cover is shown in the open position.

DETAILED DESCRIPTION OF THE INVENTION

A preferred embodiment of a gas permeable culture flask in accordance with the present invention is shown generally at 10 in FIG. 1. The culture flask includes flask 12 which is a conventional cell culturing flask which is preferably made from impact resistant plastic or glass which is gas impermeable, optically clear, non-toxic and inert with respect to the cells to be cultured.

The flask 12 includes gas impermeable walls 14 which have a total surface area which can be determined from the dimensions of the particular flask being used. The flask walls 14 define a culturing zone 16. The culturing zone 16 will typically have an atmosphere containing one or more gases. The atmosphere within the culturing zone 16 prior to introduction of cells and culturing fluid and subsequent placement into the controlled atmosphere incubator is usually air but may include other gases such as carbon dioxide, nitrogen or rare gases such as argon.

The flask 12 includes a neck 18 which is threaded to receive a cap 20. The neck 18 is integral with the flask and defines a cylindrical conduit having one end integral with the flask and the other end defining an opening through which the cells and culture fluids may be introduced into the culturing zone. The neck 18 and the cap 20 constitute one of a number of well known means for introducing mammalian cells and culture fluids into culturing zone 16. As is conventionally known, the cap 20 is unscrewed from neck 18 to provide an opening through which cells and culturing fluids can be introduced into the flask. The cap 20 is subsequently screwed back onto neck 18 to re-seal the flask.

In accordance with the present invention, a gas permeable insert 22 as best shown in FIG. 2 is provided in cap 20. The gas permeable insert may be made from any suitable gas permeable material so long as it provides free passage of gases such as oxygen and carbon dioxide into the culturing zone 16 while preventing bacteria and fungi from passing therethrough. Several gas-permeable plastic materials having suitable pore size sufficient to permit free passage of oxygen and carbon dioxide while preventing passage of bacteria and fungi are available. These plastics include Celgard, a product of the Celanese Corporation and Nuclepore and Milipore GS membranes which are available from Nuclepore Corporation and Millipore Corporation respectively. The gas permeable plastic preferably will have an average pore size which is less than 0.2 microns, but not less than 0.01 microns. Plastics or other membrane materials with pore sizes within this range are preferred since they provide adequate rates of carbon dioxide and oxygen permeability while preventing passage of microorganisms.

As a particular feature of the present invention, a flap or cover 24 is provided which is hinged to the cap 20 as shown at 26. The cap 24 is shown in FIG. 1 in the closed position. The cap 26 is preferably left in the closed position when the flask 10 is outside of the controlled atmosphere of the incubator. Whenever the flask 10 is placed within the controlled atmosphere of the incubator, the cover 24 is opened as shown in FIG. 2 to allow communication between the gases in the incubator atmosphere and the culturing zone 16 to provide rapid and uniform equilibration. The gas permeable culture flask shown generally at 28 in FIGS. 3 and 4 is an alternate preferred embodiment in accordance with the present invention. The gas permeable culture flask 28 includes flask 30 which is basically the same as flask 12 shown in FIGS. 1 and 2 except that a gas permeable insert 32 (See FIG. 4) is provided in a wall 34 of the flask 30. The gas permeable insert 32 is made from the same gas permeable materials used for insert 22. The gas permeable insert 32 is selectively occluded by cover or flap 36. The cover 36 is hinged to the flask 30 as shown at 38 by conventional means. The cover 36 is shown in the closed position in FIG. 3 where it is preferably placed when the flask 28 is outside of the controlled atmosphere of the incubator. In FIG. 4, the cover 36 is shown in the open position where it is preferably placed when the flask is inside the controlled atmosphere of the incubator to provide rapid and uniform equilibration between the gases in the incubator and the flask.

As another feature of the present invention, a gas permeable insert may be placed within the cap or wall of the flask without the necessity of providing a cover if the surface area of the gas permeable membrane (having pore sizes within the above described ranges and having the resulting flow-through rates) is limited to below approximately 3% of the overall surface area of the flask. Flasks having gas permeable inserts within this particular surface area range can be left outside the controlled atmosphere of an incubator for extended times of up to about 40 minutes without substantial loss of desired gases and resultant changes in culture pH.

The gas permeable culture flask in accordance with the present invention is especially well suited for use in combination with incubators having controlled atmospheres in which the carbon dioxide level is maintained at between 5 and 7 volume percent. As previously mentioned, the use of such constant carbon dioxide atmosphere incubators is well known and commonly used in combination with bicarbonate suffering systems utilized to maintain tissue culture fluids at physiologic pH levels. Although the gas permeable flask in accordance with the present invention may have other uses with cell culturing systems in which gas permeabillity of the flask is desired, the present invention is especially well-suited for use in the constant carbon dioxide atmopshere incubators where it is desirable to prevent the escape of carbon dioxide from the culture flask when it is removed from the incubator in order to maintain the bicarbonate buffering system within the tissue culture fluid at or near the desired pH of 7.4.

Examples of practice demonstrating the present invention are as follows:

In the following examples, standard tissue culture techniques (Willmer, E. N., editor: Cells and Tissues in Culture. Methods, Biology and Physiology 1. London 1965) were used. Commercially available gas impermeable mammalian tissue culture flasks from various manufacturers were modified by an insert of gas-permeable plastic (GPP) placed in the body of the flask or in its cap. The gas-permeable plastic, Celgard, a product of the Celanese Corporation, was used in the initial studies. In subsequent studies Nuclepore and Millipore GS$^R$ membranes available from Nuclepore Corporation and Millipore Corporation were used.

EXAMPLE 1

Dulbecco modified Eagle's medium (DMEM) at pH 7.98 in a volume of 100 ml or 40 ml was placed into either Falcon T-175 flasks available from Falcon Labware or Lux T-75 flasks available from Lab-Tek Division, Miles Laboratories, Inc. Flasks were either unmodified or contained an insert of Celgard polypropylene 2402 over an opening of between 2.3 and 9 cm$^2$. Flasks were placed in a standard $CO_2$ tissue culture incubator with a flow of $CO_2$ sufficient to maintain the concentration of 5%. After 6 hours the $CO_2$ concentration was increased to 7.5%. Samples of DMEM were removed at intervals and their pH determined. As shown in Table 1, equilibration to physiologic levels of tissue culture pH occurred much more rapidly in flasks with a GPP insert than in standard flasks. The rate of equilibration was a function of the ratio of the surface area of GPP to the surface area of the liquid in the flask except at high ratios of the surface area of the GPP to the surface area of the flask.

TABLE 1

| Flask | Celgard$^R$ membrane | Vent size (cm$^2$) | Vent: surface area ratio | Time to equilibrium (minutes) |
|---|---|---|---|---|
| Nucleon T-175 | 2402 | None | 0 | >480 |
| Nucleon T-175 | 2402 | 2.25 | .013 | >105 |
| Nucleon T-175 | 2402 | 4 | .023 | ≦105 |
| Nucleon T-175 | 2402 | 9 | .051 | <105 |
| Lux T-75 | 2402 | None | 0 | >480 <1260 |
| Lux T-75 | 2402 | 2.4 | .032 | <105 |
| Lux T-75 | 2402 | 4 | .053 | <105 |
| Lux T-75 | 2402 | 5.8 | .077 | <105 |

EXAMPLE 2

This example is similar to that of example 1, except that Corning T-25 flasks were used and holes of 0.3 to 0.4 cm$^2$ in the caps were covered with Celgard K443, Nuclepore 0.2 micron or Millipore GS 0.22-micron membranes. The results shown in Table 2 indicate a more rapid pH equilibration of the contents of the flasks containing caps with gas-permeable membranes.

TABLE 2 pH Equilibration of DMEM in T-25 Flasks with Caps Containing a 0.3 to 0.4 cm$^2$ Hole Covered by Gas-permeable Membrane

| Cap | % $CO_2$ | T = O | pH 45 min. | pH 60 min. |
|---|---|---|---|---|
| Standard | 12 | 8.16 | 7.47 | — |
| Celgard K443 | 12 | 8.16 | 7.09 | — |
| Nuclepore | 12 | 8.16 | 7.15 | — |
| Millipore GS$^R$ | 12 | 8.16 | 7.23 | — |
| Standard | 4 | 8.16 | — | 8.11 |
| Celgard K443 | 4 | 8.16 | — | 7.37 |
| Nuclepore | 4 | 8.16 | — | 7.22 |
| Millipore GS$^R$ | 4 | 8.16 | — | 7.24 |

EXAMPLE 3

This example demonstrates the growth of a hardy cell line in gas permeable culture flasks in accordance with the present invention under conditions of optimal pH maintenance in the culture.

The human promyelocytic cell line, HL-60, in a volume of 25 ml and alpha-medium without antibiotics and at a concentration of $8 \times 10^5$ cells/ml in volumes of 25 ml, was introduced into Lux T-75 flasks. These flasks were either standard as received from the manufacturer or modified by the introduction of a 2.3 cm$^2$ hole covered by Celgard GPP (manufacturer number 2402 or K443). Before introduction into the flask, the pH was carefully equilibrated to 7.4. The cells were incubated for 72 hours in a standard water jacket incubator with an atmosphere having a carbon dioxide level of 5 volume percent. Cell number was determined after 72 hours. As shown in Table 3, there was clearly no inhibition of cell growth in flasks containing gas-permeable plastic inserts.

TABLE 3

Effect of Gas-permeable Membranes on HL-60 Cell Growth in Alpha Medium at pH 7.4 in T-75 Lux Flasks

| Flask No. | Membrane (Celgard$^R$) | Surface area (cm$^2$) | Cell number at 3 days* 10$^5$/ml |
|---|---|---|---|
| 1 | None | — | 17.0 |
| 2 | None | — | 18.6 |
| 3 | 2402 | 1.3$^2$ | 12.6 |
| 4 | 2402 | 1.3$^2$ | 19.4 |
| 5 | 2402 | 1.3$^2$ | 19.4 |
| 6 | K443 | 1.5$^2$ | 18.4 |
| 7** | 2402 | 6 | 22.4 |
| 8** | 2402 | 6 | 21.6 |

*$8 \times 10^5$/ml inoculated
**Culture of *E. coli* C600 placed on membrane

EXAMPLE 4

To establish whether the GPP inserts could serve as a barrier against microbial contamination, two flasks from the series described in Example 3 were modified by gluing a small plastic ring (internal diameter 1 cm) onto the GPP insert in the culture flask. At the time of introduction of flasks into the incubator, an actively growing culture of *E. coli* (approximately 0.3 ml) was introduced into the small chamber defined by the glued plastic ring. Cell culture inside the flask and the microbial culture on the outside of the flask which were separated by the GPP were grown for 72 hours. The observed result was that the HL-60 cells continued to grow unimpeded and without bacterial contamination by the *E. coli*.

EXAMPLE 5

A second example follows which establishes the effectiveness of GPP as a barrier against two other types of microbial contamination. The caps of Corning T-25 flasks were modified by the placement of a central hole approximately 4 mm in diameter. The hole was covered by Celgard polypropylene K443 membrane. This was glued in place to provide a gas-permeable barrier. Alpha-medium containing 10% fetal calf serum and without antibiotics in a volume of 5 ml was placed in standard T-25 flasks that had the modified caps. These were introduced into a standard $CO_2$ incubator, and over a period of 24 hours an aerosol of either a Serratia species or Staphylococcus aureus 502A was introduced into the incubator. The flasks were then tightly stopped with standard caps and observed over a subsequent 4-day period for evidence of contamination. None was observed.

EXAMPLE 6

The following example demonstrates the effectiveness of gas-permeable plastic inserts in accordance with the present invention as barriers against fungal contamination. Corning T-25 flasks whose caps were modified as in Example 5 and containing 10 ml of F12 medium plus 10% fetal calf serum without antibiotics were introduced into a standard $CO_2$ incubator with an aerosol of *Candida albicans* over a period of 72 hours. Incubation was continued for an additional 5 days. No growth of *C. albicans* within the flask occurred.

EXAMPLE 7

Various cell lines were suspended in DMEM with 10% fetal calf serum at pH 8.11 at a concentration of $1 \times 10^5$/ml, and 5 ml volumes were dispersed in Corning T-25 flasks with standard caps or caps with holes of approximately 4 mm diameter covered y Celgard K443 gas-permeable plastic. Standard caps were loosely screwed on the flasks, and modified caps were screwed down tightly. Flasks were placed in a standard 37° C. incubator with a $CO_2$ concentration of 5%. Incubation was continued 5 to 7 days. At that time cells were collected by incubating with Trypsin, and counted. Cell lines included normal rat kidney (NRK), NRK cells transformed by Harvey murine sarcoma virus (Ha-NRK), NRK cells transformed by Kirsten sarcoma virus (Ki-NRK), murine 3T3 cells transformed by Rous sarcoma virus (Src-3T3), and rat cells transformed by feline sarcoma virus (CL10) cells. The results are shown in Table 4 and indicate modestly to greatly enhanced growth in flasks with caps modified by gas-permeable plastics. Src-3T3 cells, for example, grow much better when pH is rapidly restored to and maintained at physiologic levels in flask modified with gas-permeable filters.

TABLE 4

Growth of Cells Inoculated at $5 \times 10^5$/Flask in DMEM at pH 8.11 in Standard Flasks or Flasks with Caps Modified by a Hole Covered by Celgard Gas-permeable Plastic

| | Cell number at 5 days in flasks with | |
|---|---|---|
| Cell line | Standard caps | Caps with gas-permeable plastics |
| NRK | $1.27 \times 10^6$ | $1.88 \times 10^6$ |
| Ha-NRK | $2.6 \times 10^5$ | $5.5 \times 10^5$ |
| Src-3T3 | $0.6 \times 10^5$ | $20.4 \times 10^6$ |
| CL10 | $4.6 \times 10^6$ | $8.4 \times 10^6$ |
| Balb 3T3 | $8.9 \times 10^5$ | $45.3 \times 10^5$ |

EXAMPLE 8

This example demonstrates the effect of gas-permeable plastics on loss of carbon dioxide and rise in pH when tissue culture flasks are removed from a carbon dioxide incubator and exposed to ambient conditions. Lux T-75 flasks, either conventional or containing a GPP insert, were equilibrated overnight in a carbon dioxide incubator (7% $CO_2$), then placed in a horizontal position in a Biogard hood. Samples of medium (Dulbecco's modified Eagle's containing 10% fetal calf serum) were removed at intervals for determination of pH. The results, shown in Table 5, indicate that unobstructed GPP inserts allow undesirably rapid loss of $CO_2$ from the medium and rise in pH.

TABLE 5

RISE IN pH IN FLASKS CONTAINING AN INSERT OF GAS-PERMEABLE PLASTIC (GPP) REMOVED FROM A $CO_2$ INCUBATOR AND PLACED IN A TISSUE CULTURE HOOD (BIOGARD$^R$)

| Flask no. | Area covered by gas-permeable plastic* (cm²) | Ratio of GPP area to bottom surface of flask | Ratio of GPP area to total surface area of flask | pH at 0 time | pH at 20 min | pH at 38.5 min |
|---|---|---|---|---|---|---|
| 1 | 0 | 0 | 0 | 7.20 | 7.20 | 7.20 |
| 2 | 3.8 | .05 | .015 | 7.20 | 7.37 | 7.75 |
| 3 | 7.5 | .10 | .030 | 7.20 | 7.43 | 7.86 |
| 4 | 15 | .20 | .060 | 7.20 | 7.47 | 7.88 |
| 5 | 30 | .40 | .120 | 7.20 | 7.61 | 8.15 |

*Celgard K443$^R$

In order to achieve acceptably long working conditions outside of a carbon dioxide incubator, inserts of GPP in accordance with the present invention either must be small relative to the surface area of the flask or must be occluded by a gas-impermeable barrier. Gas-permeable inserts with pore sizes of approximately 0.1 micron or greater must be less than or equal to 3% of the total surface area of the flask to allow sufficient working time outside a carbon dioxide incubator. Flasks containing larger surface areas of gas-permeable plastics (see, for example, U.S. Pat. No. 3,870,602 Gas Permeable Sterile Culture Bottles which was discussed in the Background of the Invention) would be unsatisfactory for culture and handling of mammalian cells, although they might be useful for the culture of microorganisms.

Tissue culture flask walls or their caps, modified by an insert of gas-permeable plastics in accordance with the present invention, are closed systems that deny entry to microorganisms and that permit rapid equilibration of carbon dioxide concentrations between the contents of the flask and the external environment. Gas-permeable plastics provide an effective barrier to bacterial and fungal contamination of tissue culture cells while permitting better-than-standard maintenance of optimal pH conditions within the flasks when they are placed within the carbon dioxide incubator. Flasks with gas-permeable plastic inserts permit better growth of most cell lines if the initial cell inoculation is in alkaline tissue culture medium—a condition frequently prevailing under conditions of routine tissue culture. The modified flasks are superior to conventional flasks for the routine culture of mammalian cells. In accordance with the present invention, the ratio of the surface area of the gas-permeable plastic insert should not exceed approximately 3% of the surface area of the flask, in order to provide sufficient working time outside of the carbon dioxide incubator or the flask should include means for selectively occluding passage of gas through the gas permeable insert as shown in FIGS. 1-4.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is limited only by the following claims.

What is claimed is:

1. A gas permeable culture flask adapted for use in growing cell cultures in incubators having controlled atmospheres with selected levels of one or more gases, said flask comprising:
   a flask having a unitary body including gas impermeable walls with a surface area defining a culturing zone having an atmosphere containing one or more gases;
   a neck connected to said flask body having an opening for introducing mammalian cells and culture fluids into said culturing zone to form a cell culture within said culturing zone;
   a gas permeable insert located in said flask wall defining a gas permeable opening through which said gases from the atmosphere in said incubator can communicate with the gases in the atmosphere in said flask to thereby allow equilibration between the two atmospheres while the flask is in said incubator to form an equilibrated atmosphere in said flash which is substantially equivalent to the atmosphere in said incubator having said selected levels of one or more of said gases, said selected levels of gases being chosen to provide the desired growth of said cell culture, said gas permeable insert being made from material having a sufficiently large pore size to allow passage of said gases therethrough while having a sufficiently small pore size to prevent microorganisms from passing therethrough;
   means associated with said flask for selectively occluding said gas permeable insert, said occluding means being movable repeatedly between an open position when said flask is placed within said incubator to allow exchange of gases through said gas permeable insert and a closed position when said flask is removed form said incubator atmosphere to prevent the escape of gases from said culturing zone through said gas permeable insert to thereby increase the amount of time said flask may be left outside said incubator atmosphere while still maintaining the desired selected levels of gases within the atmosphere of said flask;
   a cap for covering said opening in said neck; and
   means for removably mounting said cap to said neck whereby said cap may be removed from said neck when said cells and culturing fluids are to be introduced into or removed from said culturing zone.

2. A gas permeable culture flask according to claim 1 wherein said means for removably mounting said cap includes a threaded portion on said flask neck and a mating threaded portion on said cap to provide screw type mounting of said cap to said flask neck.

3. A gas permeable culture flask according to claim 1 wherein a gas permeable insert is also located in said cap and wherein means associated with said cap are also provided for selectively occluding said gas permeable insert located in said cap.

4. A gas permeable culture flask according to claim 1 where said means for occluding said gas permeable insert includes a gas permeable cover which is of sufficient size to substantially cover said gas permeable insert and means for providing selective and repeatable movement of said cover between a closed position covering said gas permeable insert to prevent passage of gas therethrough and an open position displaced away from said gas permeable insert to allow passage of gases therethrough.

5. A gas permeable insert according to claim 4 wherein said gas impermeable cover is hinged to said flask adjacent said gas permeable insert to allow hinged movement of said cover between the position covering said gas permeable insert and the position displaced away from said gas permeable insert.

6. A gas permeable culture flask adapted for use in growing cell cultures in incubators having controlled atmospheres with selected levels of one or more gases, said flask comprising:
   a flask having a unitary body including gas impermeable walls with a surface area defining a culturing zone having an atmosphere containing one or more gases;
   a neck connected to said flask body having an opening for introducing mammalian cells and culture fluids into said culturing zone to form a cell culture within said culturing zone;
   a cap for covering said opening in said neck; and
   means for removably mounting said cap to said neck whereby said cap may be removed from said neck when said cells and culturing fluids are to be introduced into or removed from said culturing zone;
   a gas permeable insert located in said cap defining a gas permeable opening through which said gases from the atmosphere in said incubator can communicate with the gases in the atmosphere in said flask to thereby allow equilibration between the two atmospheres while the flask is in said incubator to form an equilibrated atmosphere in said flask which is substantially equivalent to the atmosphere in said incubator having said selected levels of one or more of said gases, said selected levels of gases being chosen to provide the desired growth of said cell culture, said gas permeable insert being made from material having a sufficiently large pore size to allow passage of said gases therethrough while having a sufficiently small pore size to prevent microorganisms from passing therethrough;
   means associated with said flask for selectively occluding said gas permeable insert, said occluding means being movable repeatedly between an open position when said flask is placed within said incubator to allow exchange of gases through said gas permeable insert and a closed position when said flask is removed form said incubator atmosphere to prevent the escape of gases from said culturing zone through said gas permeable insert to thereby increase the amount of time said flask may be left outside said incubator atmosphere while still maintaining the desired selected levels of gases within the atmosphere of said flask.

7. A gas permeable culture flask according to claim 6 wherein said means for removably mounting said cap includes a threaded portion on said flask neck and a mating threaded portion on said cap to provide screw type mounting of said cap to said flask neck.

8. A gas permeable culture flask according to claim 6 wherein a gas permeable insert is also located in said flask wall and wherein means associated with said flask wall are also provided for selectively occluding said gas permeable insert located in said flask wall.

9. A gas permeable culture flask according to claim 6 where said means for occluding said gas permeable insert includes a gas impermeable cover which is of sufficient size to substantially cover said gas permeable insert and means for positioning said cover in a closed position covering said gas permeable insert to prevent passage of gas therethrough and an open position displaced away from said gas permeable insert to allow passage of gases therethrough.

* * * * *